United States Patent [19]

Wands et al.

[11] 4,271,145

[45] Jun. 2, 1981

[54] PROCESS FOR PRODUCING ANTIBODIES TO HEPATITIS VIRUS AND CELL LINES THEREFOR

[75] Inventors: Jack R. Wands, Waban, Mass.; Vincent R. Zurawski, Jr., West Chester, Pa.

[73] Assignee: The Massachusetts General Hospital, Boston, Mass.

[21] Appl. No.: 86,947

[22] Filed: Oct. 22, 1979

[51] Int. Cl.³ .................... A61K 39/00; A61K 39/42; C12N 1/26
[52] U.S. Cl. ........................................ 424/85; 424/86; 424/88; 424/89; 435/240; 435/948
[58] Field of Search ................. 424/85, 86; 435/2, 68, 435/240, 948

[56] References Cited

U.S. PATENT DOCUMENTS 4,196,265  4/1980  Koprowski et al. .................... 424/86

OTHER PUBLICATIONS

The Lancet, editorial, pp. 1242–1243, Jun. 11, 1977.
Koprowski et al., Proc. Natl. Acad. Sci., USA, vol. 74, pp. 2985–2988, 1977.
Kohler and Milstein, Eur. J. Immunol., vol. 6, pp. 511–519, 1976.
Milstein & Kohler, "Antibodies In Human Diagnosis and Therapy", edited by Haber & Krause, (Raven), pp. 271–278, 1977.

*Primary Examiner*—Delbert R. Phillips
*Assistant Examiner*—Blondel Hazel
*Attorney, Agent, or Firm*—Paul J. Cook; Marvin C. Guthrie

[57] ABSTRACT

Cell lines for producing monoclonal antibodies to hepatitis virus are established by immunizing animal lymphocytes with hepatitis antigen to form antibody producing cells which then are fused with myeloma cells. The resultant somatic cell hybrids can be cloned. These clones produce monoclonal antibodies to individual antigenic determinates unique to hepatitis virus.

13 Claims, 5 Drawing Figures

PROCESS FOR PRODUCING ANTIBODIES TO HEPATITIS VIRUS AND CELL LINES THEREFOR

BACKGROUND OF THE INVENTION

The invention described herein was made during the course of work under grants from the Department of Health, Education and Welfare.

This invention relates to a process for producing antibodies to hepatitis virus and to the cell lines capable of producing such antibodies continuously.

Hepatitis viruses (type A, B and non-A, non-B agents) cause significant morbidity and mortality in man. Not only do these agents produce acute infection of variable clinical severity but they also lead to or contribute to chronic liver disease terminating in cirrhosis of the liver, parenchymal liver failure and death. This acute and chronic hepatitis infection is a major medical problem in the United States and worldwide. It is also noteworthy that chronic hepatitis infection has been associated with primary hepatocellular carcinoma in endemic areas of the world. Efforts to understand the biology of these viruses including early diagnosis by improved serologic technique and the development of prophylactic measures to prevent spread has important medical implications.

Although monoclonal antibodies have been produced to viruses other than hepatitis virus, i.e. influenza and rabies, major histocompatability antigens, red blood cells, haptens, proteins, enzymes and cell associated antigens, no accounts of production are by somatic cell hybrids of monoclonal antibodies to the human hepatitis virus or viral antigens exist. It has been proposed to utilize fused cell hybrids of BALB/c spleen cells and BALB/c myeloma cells to form antibody, e.g. Kohler et al in Eur. J. Immunol., Vol. 6, 511–519 (1976) and Nature, Vol. 256, pp. 495–497 (1975). The prior art also discloses the formation of BALB/c (P3×63 Ag8) myeloma cells derived from MOPC/21 line by Kohler et al, Nature, Vol. 256, pp. 495–497 (1975).

It would be highly desirable to provide a means for producing antibody to hepatitis virus and active derivatives to hepatitis virus. Such antibodies would be important in that they could be utilized to diagnose hepatitis viral infections in humans. Moreover, they might be useful as highly specific immunoprophylactic reagents in the treatment of hepatitis in humans.

SUMMARY OF THE INVENTION

In accordance with this invention, hybridoma cell lines are established which synthesize and secrete highly specific monoclonal antibodies to hepatitis virus antigens. As a first step, animal lymphocytes are immunized according to a specific immunization route and schedule to develop lymphocytes which produce monoclonal antibodies to hepatitis antigens. These lymphocytes are recovered and are fused with myeloma cells derived from the same animal species to form somatic cell hybrids. The cell hybrids then are propagated in tissue culture or in a syngeneic or immunocompromised animal for an indefinite period in order to continuously produce antibody to the immunizing hepatitis antigens.

DETAILED DESCRIPTION OF SPECIFIC EMBODIMENTS

Figure 1:
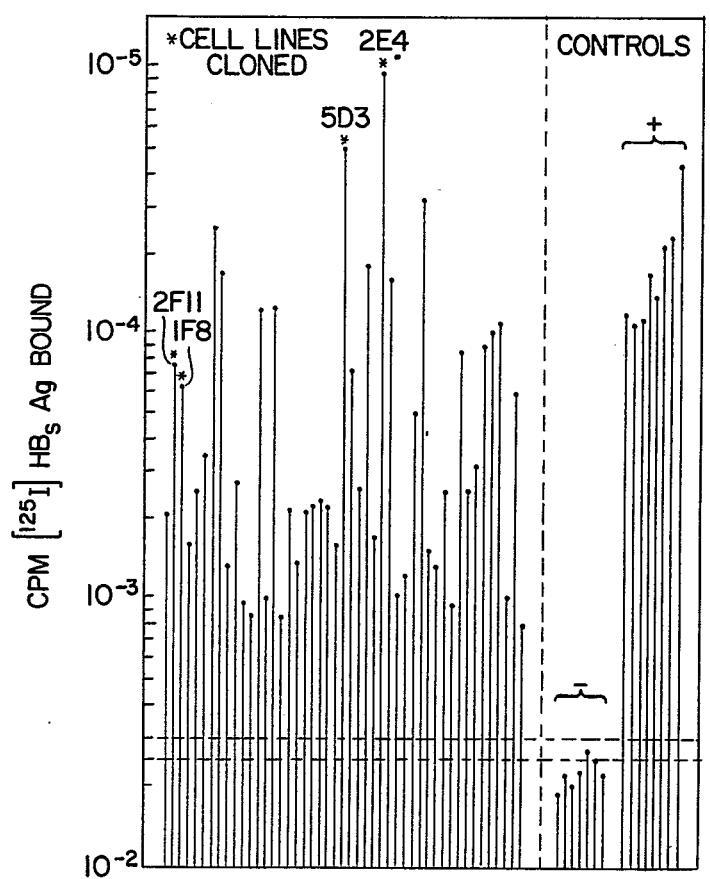

In the process of this invention, animal lymphocytes are stimulated (immunized) in vitro or in vivo by a preparation of viral antigen(s), for example hepatitis B surface antigen (HBsAg), hepatitis B e antigen (HBeAg), or antigens of hepatitis A virus (HAV), or non-A, non-B hepatitis virus(es). The route and schedule of administration of the antigen has been found to be critical to the present invention. It has been found necessary to administer the antigen first intraperitoneally followed by administering the antigen intravenously. It has been found that if both the first and second antigen doses are administered either intraperitoneally or intraveneously or if the first dose is administered intravenously and the second dosage intraperitoneally, formation of hybrid cells in successive steps is not accomplished successfully or if hybridization is accomplished, the resultant hybrids will not produce antibody continuously. In addition, it has been found that the dosage of antigen administered at each of these two steps must be maintained within certain critical limits, i.e. between approximately 1 and approximately 50 $\mu$g/animal, preferably between approximately 5 and approximately 10 $\mu$g/animal. If the dosage is too low, little or no immunization response is induced in the animal. If the dosage is too high, the animal will become tolerized to the antigen and will not produce antibody. In addition, it has been found necessary to wait at least 3 weeks, and preferably 5 or more weeks subsequent the first administration of antigen in order to administer the second dosage of antigen. If the second dosage of antigen is administered sooner than approximately 3 weeks, the immunization response is diminished in the animal. While it might be desirable to effect a separation of the antibody producing cells prior to fusion, it is not required since the separation of the antibody producing cells from the non-antibody producing cells can be effected subsequent to fusion with the myeloma cells.

Fusion with myeloma cells is effected with myeloma cells that are sensitive to hypoxanthine-aminopterin-thymidine (HAT) medium by virtue of their lacking enzymes such as thymidine kinase (TK) or hypoxanthine-guanine phosphoribosyl transferase (HGPRT). This allows selection of hybrids to be accomplished by growth in HAT medium. Myeloma cell lines utilized for cell fusions are derived from a BALB/c mouse MOPC 21 myeloma as described by Khöler et al, Eur. J. Immunol., Vol. 6, pp. 292–295 (1976). The myeloma cell line is identified as P3-NS1/1-Ag4-1. Such cells are resistant to 20 $\mu$g/ml of 8-azaguanine and die in medium containing hypoxanthine-aminopterin-thymidine (HAT). The myeloma cells are grown in a suitable cell growth medium which can be supplemented with glucose, glutamine, penicillin, streptomycin and fetal calf serum. Three other mouse lines have also been utilized for these fusions, 45.6T61.7, Sp210, and 61513. Fusion is effected by adding a suspension of the lymphocyte cells to the myeloma cells in the growth medium and centrifuging to form a pellet. The cells are then incubated in a growth medium containing the fusing agent. Suitable techniques for effecting fusion are described for example in Köhler et al, Eur. J. Immunol., Vol. 6, pp. 511–519 (1976) or Gefter et al, Somatic Cell Genet., Vol. 3, 231–236 (1977).

Hybridomas which synthesize and secrete antibodies directed toward viral antigens then are cultured to establish continuously proliferating cell lines with relatively stable genetic constitutions. The cell lines are cloned to give the progeny of individual cells from each line. The cell lines or clones are propagated indefinitely in tissue culture or in vivo in syngeneic or immunocompromised hosts where they continue to synthesize and secrete antibody to the hepatitis viral antigens. Antibody then is recovered from the tissue culture cells or from the ascites fluids or serum of histocompatable host animals by conventional precipitation, ion exchange or affinity chromatography, or the like.

The hybridomas obtained by the present invention are capable of producing either IgG antibody or IgM antibody; the latter being polyvalent. A deposit of the cell line culture identified as H25B10 is on deposit with the American Culture Collection and is assigned the ATCC accession number CRL-8017. This cell line is capable of producing IgG antibody. A deposit of the cell line culture identified as H21F8-1 is on deposit with the American Type Culture Collection and is assigned ATCC accession number CRL-8018. This latter cell line is capable of producing IgM antibody to hepatitis virus.

The following example illustrates the present invention and is not intended to limit the same.

EXAMPLE I

This example illustrates the fact that monoclonal antibodies to HBsAg can be made using the process of this invention.

Preparation of Immunizing Antigen. Hepatitis B surface antigen was isolated by density gradient sedimentation from several units of human plasma known to contain high titers of HBsAg by radioimmunoassay using methods by Bond et al, J. Infect. Desease, Vol. 125, pp. 263–268 (1972) and Dreesman et al, J. Virol., Vol. 10, pp. 469–476, (1972). Gradient fractions with the highest amount of HBsAg activity were pooled, dialyzed against phosphate buffered saline and the protein content determined by the technique derived by Lowry et al, J. Biol. Chem., Vol. 193, pp. 265–275, (1951).

Immunization of BALB/c Mice. Several issues were explored with respect to the optimal immunization procedure to produce anti-HBs secreting hybridomas which included: (1) route of primary and secondary immunizations, (2) the importance of immunizing antigen concentration and (3) the role of increasing the time interval between primary and secondary immunizations. In these studies the intraperitonial to intravenous route of antigen administration also were compared. The optimal antigen concentration (0.1, 1, 10, and 100 $\mu$g viral protein) was evaluated at the time of the second boost. Finally, the cell fusion was timed 72 hrs. following the last boost; however, the interval between the primary and secondary immunization was varied according to a 2, 3, 5 and 10 week schedule.

Preparation of Spleen Cells. Spleens were removed from immunized animals 72 hrs. following the last antigen boost and placed in Dulbecco's minimal essential medium (DMEM) supplemented with 4.5 gm/L of glucose 1000 U/ml of penicillin and 100 $\mu$g/ml streptomycin. The spleens were exhaustively teased apart with 25 gauge needles. The cells were washed $\times$3 with DMEM and resuspended at a constant concentration in the same medium. In general approximately 100 million cells were obtained from each spleen.

Preparation of Myeloma Cells. The myeloma cell line P3-NS1/1-Ag4-1 used for cell fusions was derived from a BALB/c mouse MOPC 21 myeloma as by Köhler et al, Eur. J. Immunol., Vol. 6, pp. 292–295, (1976) as described. Such cells are resistant to 20 $\mu$g/ml of 8-azaguanine and die in medium containing hypoxanthine-aminopterinthymidine (HAT). Cells were grown in DMEM supplemented with 4.5 gm/l glucose, 20 mm glutamine, 1000 U/ml penicillin, 100 $\mu$g/ml streptomycin and 20% fetal calf serum (complete medium). The myeloma cells were in the log phase of growth at the time of cell fusion.

Cell Fusion Technique. Splenocyte suspensions were added to myeloma cells in DMEM without serum at a ratio of 10:1 and centrifuged for 10 minutes at 200$\times$g to form a pellet in round bottom tubes. The medium was gently decanted off the cell mixture. Previously prepared polyethylene glycol 1000 (diluted to 30% w/w with DMEM, pH 7.6) at a volume of 2 ml was added for 6 minutes at 37° C. Following this incubation 20 ml of DMEM was added over several minutes and the cells gently resuspended. Cells were then centrifuged for 5 minutes at 200$\times$g and resuspended in complete medium to achieve a concentration of 200–300,000 cells/200 $\mu$l and plated in 100 $\mu$l aliquots in 96 well microtiter plates. Twenty four hrs. later 50 $\mu$l of medium was removed and replaced with 150 $\mu$l fresh complete medium supplemented with hypoxanthine (100 $\mu$M) and thymidine (16 $\mu$M). On day 3 there was a 50% medium change to HAT (aminopterin concentration 0.4 $\mu$M) containing complete medium. There was a subsequent 50% medium change of HAT every other day for two weeks. After this period the medium was changed daily (50%) and replaced with HT containing complete medium for 1 or 2 weeks followed by a final transfer to complete medium as the hybridomas were being grown to sufficient numbers for cloning.

Cloning of Hybridomas. All microtiter wells were initially screened positive for growth 10 to 20 days following the fusion. Once positive anti-HBs secretors were identified, cells were serially passed up to larger dishes and several hybridoma cell lines were selected for cloning. Hybridomas underwent a double dilutional cloning technique where 120 microliter wells were seeded at a calculated dilution of 0.5 cells/well on 3T3 feeder layers. The remaining positive secretors were grown up, frozen and stored under liquid nitrogen in complete medium containing 25% fetal calf serum and 7.5% dimethylsulfoxide.

Chromosone Analysis of Clones. For chromosome analysis, splenocytes, P3-NS1/1 -Ag4-1 myeloma cells and clonal hybridomas were exposed to colchicine (10 $\mu$g/ml) for 2 hrs. at 37° C., treated with hypotonic (0.075 M) KCl solution, and fixed in a 3:1 mixture of cold absolute methanol and glacial acetic acid; several drops of the cell suspensions were placed on a glass slide, air dried and stained with Giemsa's 1:50 buffered to pH 6.8 with citric-phosphate buffer.

Analysis of Anti-HBs Activity. Three separate assays were employed in the analysis for anti-HBs activity. One hundred and twenty microliters of culture supernatant was removed from the microtiter plates and diluted to 200 $\mu$l with complete medium. From a series of preliminary experiments the best incubation conditions were determined to optimize the anti-HBs binding. Hepatitis B surface antigen coated beads were incubated for 24 hours at room temperature followed by extensive washing with distilled water. [$^{125}$I]-HBsAg was added (100–150,000 cpm) and the plates incubated at room temperature for an additional 36 hr. period. The beads were again extensively washed with distilled water and counted in a Packard gamma counter.

In the second solid phase radioimmunoassay employed goat anti-mouse F(ab')$_2$ was prepared which had been affinity column purified as described by Williams et al, Cell, Vol. 12, pp. 663-673 (1977). This antibody was iodinated with [$^{125}$I] using the lactoperoxidase method described by Marchalonis, Biochem. J., Vol. 113, pp. 299-314 (1969). The procedure for this solid phase radioimmunoassay was identical to the one mentioned above except [$^{125}$I]-anti-mouse F(ab')$_2$ (100,000 cpm) was added as the second probe.

Finally the capability of anti-HBs produced by hybridomas to agglutinate HBsAg coated (ayw and adw subtypes) human 0-negative red blood cells in a microhemagglutination reaction was evaluated as described by Wands et al, Gastroenterology, Vol. 68, pp. 105-112 (1975). In brief, 25 μl of culture supernatant was diluted by 25 μl of Tris buffer, pH 7.4 and serial 2-fold dilutions were performed in 96 well V bottom microtiter plates. Twenty five microliters of a 0.5% solution of HBsAg-coupled indicator red blood cells were added and incubated at 37° C. for 45 minutes on a rocker platform (6 cycles/min). The cells were sedimented at 200×g for 10 minutes and allowed to stand at a 45° angle for 15 minutes. The titer of anti-HBs was determined as the last dilution which gave a positive agglutination reaction.

The positive controls for all assays included sera from HBsAg immunized mice at various dilutions obtained at the time of spleen removal. In addition we had available 15 well characterized hemophiliac serum which contained exceedingly high titers of anti-HBs. All such sera gave precipitation reaction with HBsAg in Ouchterlony gel diffusion, high binding in the standard radioimmunoassay and passive hemagglutination titers ranging from 1:64,000 to 1:1, 200,000. The hemophiliac serum was added undiluted in each assay. Negative controls consisted of medium from the P3-NSl/l-Ag4-l myeloma cell line, media from immunized spleen cells after 3 days in culture, media from two other hybridoma cell lines secreting monoclonal antibodies to tetanus toxoid and cardiac myosin normal mouse and human serum.

The Effect of Immunization Schedule. As shown in Table I, serum titers of anti-HBs, a reflection of the immunization protocol, increased progressively as a function of the length of time from the primary immunization to the secondary antigen boost. More importantly, although hybridomas were produced when the second antigen boost was at 2 and 3 weeks, these cells exhibited only small levels of anti-HBs activity. These low levels of anti-HBs activity were subsequently lost as the hybridomas were serially passed in tissue culture. When, however, a longer maturation time was allowed between the primary and secondary immunizations, there was not only an increase in the percent of positive anti-HBs secreting cell lines but it was possible to achieve a number of stable and continuously maintained hybridoma cell lines which have retained their very high anti-HBs secretory activity.

Analysis of Hybridomas. FIG. 1 illustrates the results from one such successful fusion under optimal immunization conditions and depicts the range of anti-HBs activity in 47 positive cell lines. The area between the parallel dotted lines in this and the other figures represents the mean ±SEM of the negative controls. In this experiment, assays for anti-HBS binding using the [$^{125}$I]-HBsAg probe were performed 10 to 20 days after the initial fusion when growth was observed in the 96 well microtiter plates. It is noteworthy that 120 μl of cell culture supernatant (total volume 200 μl/well) obtained from some hybridomas yielded extraordinarily high values for [$^{125}$I]-HBsAg binding activity. For example, anti-HBs produced by cell line 2E4 bound 95,000 of the 100,000 cpm added in the radioimmunoassay.

Figure 2:
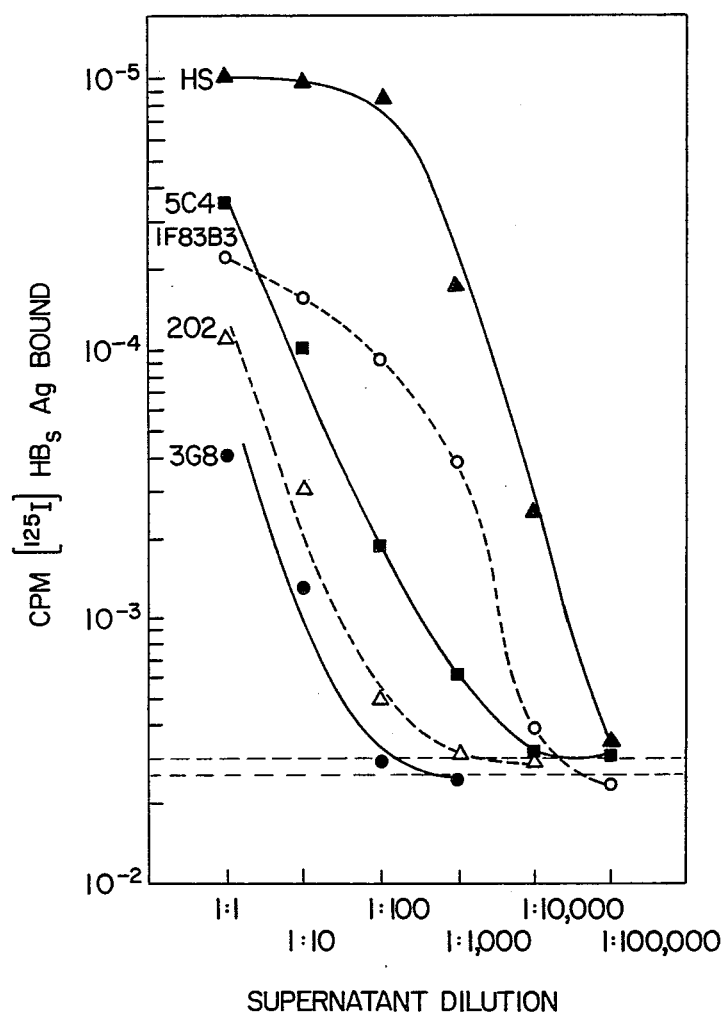

Table 2 shows some representative examples of hybridomas secreting anti-HBs as measured by the three different assays employed; each assay was confirmatory for anti-HBs production. Anti-HBs derived from some hybridoma cultures were exceptionally good agglutinating antibodies and capable of discriminating between HBsAg subtypes. For example, 1F8 and its clone 1F8-3B6 only agglutinated red blood cells coated with subtype adw and not ayw indicating no specificity either for the d determinant or some yet to be defined antigen on the adw subtype. It is noteworthy that other cell lines, namely 2G2 and 5C4 produced anti-HBs which recognized a common determinant on both subtypes; residing wither on the a or w or another commonly shared antigen. Moreover, 25 μl of culture supernatant diluted 1:256 still give a positive agglutination reaction suggesting an exceptionally high avidity of the hybridoma anti-HBs for HBsAg. Further support for this conclusion is demonstrated by the dilution curves of anti-HBs containing supernatants shown in FIG. 2. In comparison is a dilution curve of a hemophiliac serum (HS) where anti-HBs was detectable at 1:50 by Ouchterlony gel diffusion and gave a final hemagglutination titer of 1:2.2×10$^6$ for both adw and ayw coated red blood cells.

Anti-HBs produced by individual clones exhibited apparently unique heavy chain subclass as shown in Tables 4 and 6. Of the four clones examined thus far, all produced IgM with anti-HBs activity. However, the original cell lines (Table 4) produced anti-HBs of the IgG$_1$ isotype; line 2F2 both IgG$_1$ and IgG$_{2b}$ and line 2C4, IgG$_1$ and IgA. These data along with the electrophoretic data shown below gave conformation of the clonal nature of the lines.

Characteristics of the Immunoglobulin Produced by the Cloned Hybridomas

Figure 4:
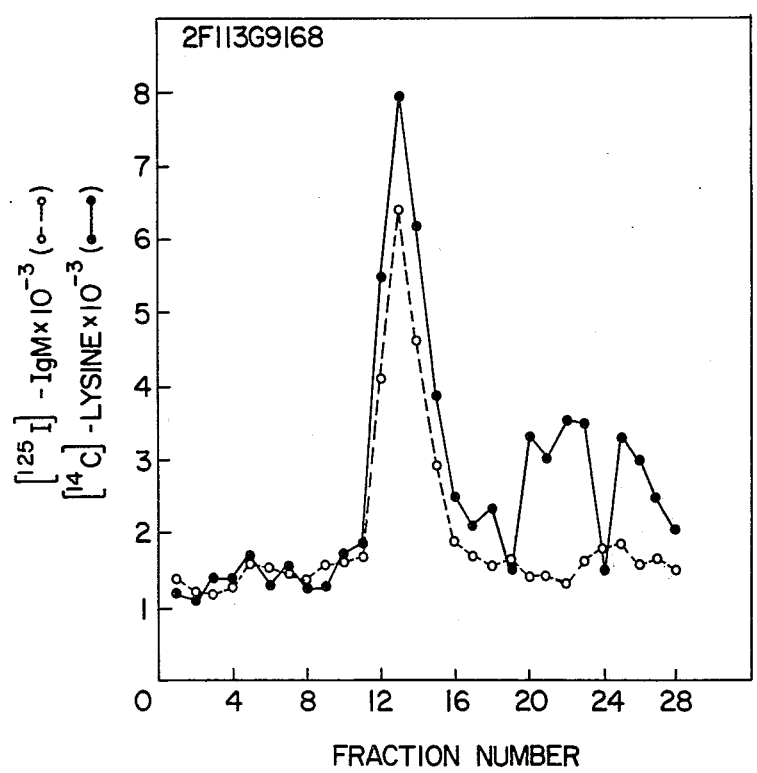
Figure 5:
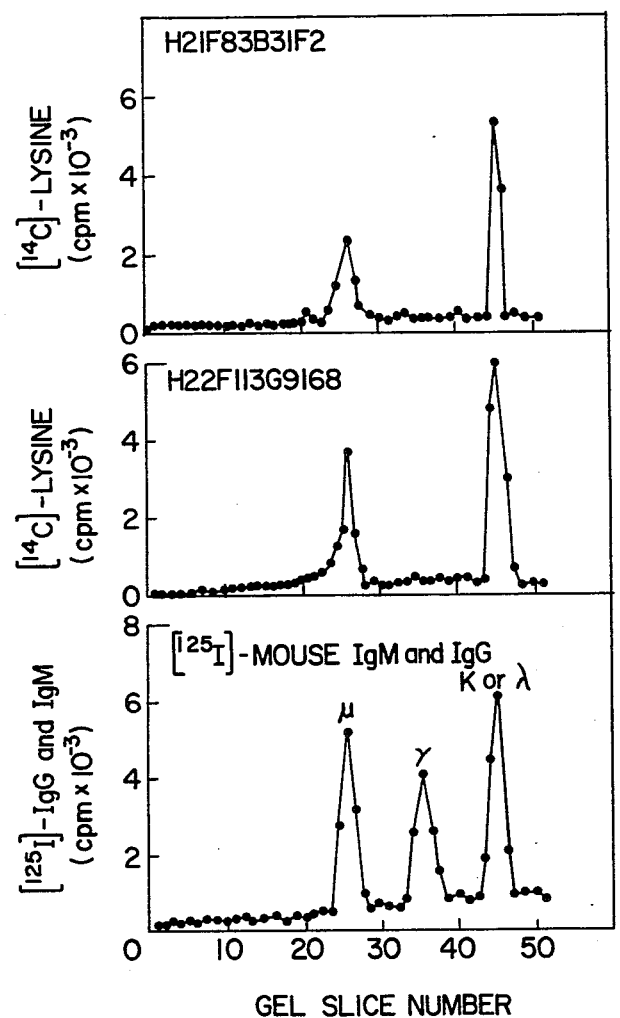

As noted above, the class and subclass of anti-HBs activity secreted by the hybrid clones were analyzed. Immunized splenocytes alone in culture did not produce anti-HBs activity by radioimmunoassay. Likewise, no anti-HBs activity was detected in culture supernatants of the P3-NSl/l-Ag4-l parent myeloma cell line (Table 5). Clonal hybridomas 2F11 and 1F8 were incubated with [$^{14}$C]-lysine and the immunoglobulin with anti-HBs activity was subjected to further analysis by Sepharose 4B column chromatography and SDS polyacrylamide gel electrophoresis. FIG. 4 depicts the results of Sepharose 4B column chromatography of [$^{14}$C]-lysine labeled culture supernatant from cloned hybridoma 2F112G91C8. As shown in FIG. 4, the immoglobulin produced by 2F11 with anti-HBs comigrated with IgM. FIG. 5 depicts SDS-polychrylamide gel electrophoresis of [$^{14}$C]-lysine labeled supernatant from clones 2F113G91C8 and 1F83B71F2 with anti-HBs activity. When the anti-HBs IgM was subjected to SDS-polyacrylamide gel only IgM heavy chain and light chain as shown in FIG. 5 were detected and no other immunoglobulin isotypes. This demonstrates that the anti-HBs activity can reside in a unique immunoglobulin isotype and results from the fusion of P3-NSl/l-Ag4-l parent myeloma and immunized splenocytes. This cell line is identified as ATCC CRL-8018. The clonal nature of the hybridomas by the criteria mentioned above therefore were established and the fact that 4 of the cloned cell lines produced anti-HBs as measured by all three binding assays.

An additional experiment was performed prior to cloning of several such cell lines to establish that these cells were indeed producing anti-HBs with very high binding activity as shown in Table 3. In this study microtiter wells were seeded at various concentrations ranging from $10^4$ to $10^2$ cells/well. Four days later each well was assayed for anti-HBs activity. As expected all wells yielded positive growth and the presence in the supernatant of very high anti-HBs activity. Thus cell lines 2F11, 1F8, 5D3 and 2E4 were selected for double cloning by using the previously described dilutional techniques.

Figure 3:
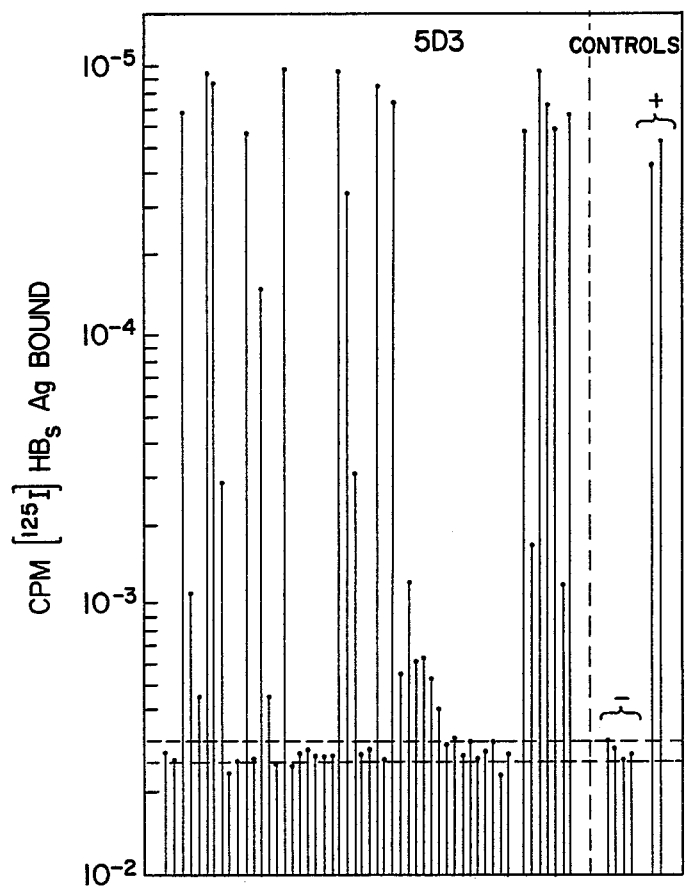

Closing of Hybridomas. FIG. 3 is a representative example of the dilutional cloning of line 5D3. Of the initial 120 wells seeded at 0.5 cells/well, 53 or 44% yielded positive hybridoma cell growth; however, only 21 of the 53 gave anti-HBs binding values greater than 1000 cpm and were considered positive anti-HBs secretors. It is noteworthy that 120 μl of culture supernatant obtained from 12 such cell lines produced anti-HBs which bound more than 50,000 of the 100,000 cpm of added [$^{125}$I]-HBsAg; these values were in excess of those obtained with hemophiliac sera. Two of the hybridomas with high anti-HBs activity (100-000 and 96,000 cpm [$^{125}$I]-HBsAg bound respectively) were recloned by the same technique and all showed 95-98% binding values (Table 4).

Further Analysis of Clones. The cloned hybridomas were subjected to chromosomal analysis and results compared to the original myeloma cell line and immunized splenocytes. The P3-NS1/1-Ag4-1 myeloma cells contained a mean number of 63 chromosomes, splenocytes, a mean number of 40, and the clones hybridomas 80 to 97 (Table 5). These results suggest that the cells secreting anti-HBs contained the expected number of chromosomes and were indeed derived from the fusion of NS1 cells and HBsAg immunized splenocytes.

TABLE 1

The effect of immunization schedule on the production of hybridomas secreting anti-HBs

|  | 2 weeks* | | 3 weeks | | 5 weeks | | 10 weeks | |
| --- | --- | --- | --- | --- | --- | --- | --- | --- |
| Mouse serum dilution | | | | | | | | |
| 1:10$^1$ | 1.60 | (14%)$^a$ | 16.0 | (28%) | 51.67 | (33%) | 70.28 | (65%) |
| 1:10$^2$ | 0.70 | ( 7%) | 8.43 | (14%) | 10.74 | (15%) | 43.61 | (40%) |
| 1:10$^3$ | 0.20 | — | 0.46 | — | 1.61 | (1.1%) | 12.94 | (12%) |
| 1:10$^4$ | 0.19 | — | 0.18 | — | 0.33 | | 0.77 | (0.71%) |
| % Wells positive for hybridomas growth | 62% | | 80% | | 73% | | 100% | |
| % Hybridomas secreting anti-HBs | 0 | | 1% | | 16% | | 100% | |

*Time of intravenous secondary immunization (10 μg HBsAg) following primary immunization (10 μg HBsAg in CFA).
$^a$cpm of [$^{125}$I]-HBsAg × 10$^{-3}$ bound. The number in parenthesis represents the percent of counts bound, calculated from the total number of [$^{125}$I]-HBsAg counts added in 200 μl.

TABLE 2

Representative examples of anti-HBs activity from hybridoma supernatants as measured by three separate assays

| Number | [$^{125}$I]-HBsAg* (cpm) | [$^{125}$I]-anti-mouse F(ab')$_2$* (cpm) | Hemagglutination titer$^a$ | |
| --- | --- | --- | --- | --- |
| | | | adw | ayw |
| 1F8 | 23.06 | 4.76 | 1:256 | neg |
| 1F8-3B6$^b$ | 22.51 | 4.03 | 1:128 | neg |
| 1F8-3C2$^b$ | 3.05 | 4.54 | neg | neg |
| 2G2 | 26.03 | 10.10 | 1:64 | 1:64 |
| 2D2 | 11.52 | 8.18 | 1:32 | neg |
| 3E6 | 1.71 | 4.16 | neg | neg |
| 3G8 | 4.01 | 6.06 | 1:64 | neg |
| 5C4 | 34.35 | 1.78 | 1:256 | 1:256 |
| Media$^c$ | 0.17 | 0.53 | neg | neg |
| Neg cont$^d$ | 0.29 | — | — | — |
| Pos cont$^e$ | 43.01 | — | 1:64 | 1:64 |

*cpm of [$^{125}$I]-HBsAg and [$^{125}$I]-goat anti-mouse F(ab')$_2$ × 10$^{-3}$ bound (see materials and methods). Initial sample volume was 120 μl.
$^a$Hemagglutination titer of HBsAg coated human-negative red blood cells (HBsAg subtypes adw and ayw). Positive titers are considered 1:2. Initial sample volume was 25 μl. neg = no hemagglutination
$^b$Clones of 1F8
$^c$Mean cpm from culture medium (DMEM)
$^d$Mean cpm from medium containing clone 2B8B3 which is a hybridoma clone that produces monoclonal antibodies to tetanus toxoid.
$^e$Hemophiliac serum or Abbott standard control serum.

TABLE 3

Anti-HBs activity of hybridoma cell lines 1F8, 2F11, and 5D3 following dilutional platting

| Cell line | No. of wells seeded | No. wells pos. anti-HBs | cpm[$^{125}$I]-HBsAg bound$^a$ (mean SEM) | | |
| --- | --- | --- | --- | --- | --- |
| | | | 10$^{4*}$ | 10$^3$ | 10$^2$ |
| 1F8 | 60 | 60 | 29.33 ± 0.71 | 28.9 ± 1.06 | 19.36 ± 1.74 |
| 2F11 | 60 | 60 | 26.42 ± 0.43 | 26.12 ± 0.63 | 13.86 ± 0.80 |
| 5D3 | 60 | 60 | 88.98 ± 1.64 | 99.99 ± 3.26 | 66.07 ± 3.50 |

*The number of cells seeded/well
$^a$cpm [$^{125}$I]-HBsAg × 10$^{-3}$ bound

TABLE 4

Characterization by Isotypic Analysis of anti-HBs Produced by the Original Cell Lines and Cloned Hybridomas

| No. | Cell Line | HBsAg* | IgG$_1$$^a$ | IgG$_{2b}$$^a$ | IgA$^a$ | IgM$^a$ |
| --- | --- | --- | --- | --- | --- | --- |
| 1 | 1C3$^b$ | 1.56 | 50.70 | 0.12 | 0.09 | 0.39 |
| 2 | 1C4 | 7.20 | 4.54 | 0.16 | 0.14 | 7.33 |
| 3 | 1C6 | 8.54 | 1.51 | 0.46 | 0.18 | 16.67 |
| 4 | 1C7 | 1.23 | 47.88 | 0.14 | 0.10 | 0.33 |
| 5 | 1F2 | 11.95 | 4.46 | 27.87 | 0.09 | 0.61 |
| 6 | 1G8 | 3.83 | 23.78 | 4.95 | 0.09 | 0.73 |
| 7 | 2B10 | 2.16 | 60.63 | 0.17 | 0.12 | 0.36 |
| 8 | 2C4 | 8.23 | 55.89 | 0.15 | 0.94 | 0.51 |
| 9 | 2D11 | 4.75 | 0.49 | 0.98 | 0.44 | 6.04 |
| 10 | 2E7 | 15.70 | 0.18 | 0.09 | 0.94 | 13.10 |
| 11 | 2F11 | 22.70 | 0.55 | 0.11 | 0.14 | 9.34 |
| 12 | 3C4 | 1.95 | 50.97 | 0.15 | 0.13 | 2.14 |
| 13 | 3F9 | 2.30 | 70.44 | 0.20 | 0.09 | 0.38 |
| 14 | 3G4 | 1.72 | 49.03 | 0.09 | 0.09 | 4.22 |
| 15 | 4B2 | 5.90 | 52.01 | 0.19 | 0.70 | 15.67 |
| 16 | 4B4 | 13.30 | 0.85 | 0.12 | 0.12 | 15.95 |
| 17 | 4B6 | 1.02 | 62.50 | 0.16 | 0.08 | 0.76 |

TABLE 4-continued

Characterization by Isotypic Analysis of anti-HBs Produced by the Original Cell Lines and Cloned Hybridomas

| No. | Cell Line | HBsAg* | IgG$_1$$^a$ | IgG$_{2b}$$^a$ | IgA$^a$ | IgM$^a$ |
|---|---|---|---|---|---|---|
| 18 | 4E8 | 10.50 | 56.80 | 0.20 | 0.09 | 0.30 |
| 19 | 5B5 | 0.94 | 37.70 | 0.11 | 0.08 | 0.32 |
| 20 | 5B8 | 9.20 | 53.45 | 0.10 | 0.07 | 0.40 |
| 21 | 5B10 | 4.26 | 32.23 | 0.17 | 0.12 | 3.26 |
| 22 | H21F83B71F2$^c$ | — | 0.22 | 0.12 | 0.11 | 15.57 |
| 23 | H21F83T32C6 | — | 0.24 | 0.12 | 0.14 | 18.67 |
| 24 | H21F83T32C2 | — | 0.24 | 0.08 | 0.12 | 15.28 |
| 25 | H21F83B7$^d$ | 36.20 | 0.20 | 0.12 | 0.13 | 12.85 |
| 26 | H21F83T33B3 | — | 0.22 | 0.12 | 0.13 | 12.16 |
| 27 | H21F83B71C7 | 48.00 | 0.20 | 0.08 | 0.13 | 12.55 |
| 28 | H21F83B71F2 | 37.42 | 0.24 | 0.12 | 0.10 | 13.30 |
| 29 | H21F83B71E4 | 37.20 | 0.19 | 0.08 | 0.10 | 13.12 |
| 30 | H22F113G91B4 | 50.00 | 0.24 | 0.12 | 0.14 | 13.34 |
| 31 | H22F113G91C8 | 58.20 | 0.21 | 0.13 | 0.17 | 13.72 |
| 32 | H22F112G9 | 36.27 | 0.24 | 0.18 | 0.09 | 8.20 |
| 33 | H25D32B8 | 86.00 | 0.20 | 0.11 | 0.15 | 19.27 |
| 34 | H25D3264 | 94.06 | 0.23 | 0.16 | 0.15 | 19.25 |
| 35 | H25D32B8 | — | 0.18 | 0.14 | 0.16 | 17.80 |
| | Neg. Med.$^e$ | | 0.24 | 0.16 | 0.09 | 0.10 | 0.28 |

*cpm of [$^{125}$I]-HBsAg × 10$^{-3}$ bound in a solid phase radioimmunoassay.
$^a$cpm of [$^{125}$I]-goat anti-mouse IgG$_1$, IgG$_{2b}$, IgA and IgM × 10$^{-3}$ bound to HBsAg coated beads.
$^c$Original cell lines.
$^c$Double cloned hybridomas.
$^d$Single cloned hybridomas.
$^e$Control media added for 24 hours to HBsAg coated beads followed by the second probes and incubated for an additional 24 hours.

TABLE 5

Chromosome Analysis of Hybridomas Producing Monoclonal Anti-HBs

| Cell Type | No. Cells Examined | Mean No. Chromosomes | [$^{125}$I]-HBsAg Counts bound (mean ISEM) |
|---|---|---|---|
| NS1 | 50 | 63 | 294 ± 50 |
| Immunized* Splenocyte | 60 | 40 | 312 ± 21 |
| H22F11 | 100 | 80 | 36,261 ± 3,016 |
| H25D3 | 180 | 85 | 99,624 ± 4,068 |
| H21F8 | 100 | 97 | 53.926 ± 2,078 |

*Measurement for anti-HBs activity performed after 3 days in culture.

TABLE 6

Isotypic analysis of anti-HBs produced by cloned hybridomas

| Cell line | F(ab')$_2$* | IgG$_1$$^+$ | IgG$_{2b}$$^{30}$ | IgA$^+$ | IgM$^+$ |
|---|---|---|---|---|---|
| H21F83B71F2$^a$ | 2.44 | 0.16 | 0.14 | 0.16 | 10.12 |
| H22F113C91C8$^a$ | 2.87 | 0.15 | 0.09 | 0.09 | 12.56 |
| H22F113G91B4$^a$ | 3.34 | 0.16 | 0.12 | 0.12 | 12.80 |
| H25D32B8$^b$ | 4.43 | 0.13 | 0.13 | 0.13 | 15.21 |
| Media Cont.$^c$ | 0.26 | 0.13 | 0.07 | 0.07 | 0.18 |

*cpm of [$^{125}$I]-goat anti-mouse F(ab')$_2$ × 10$^{-3}$ bound to HBsAg coated beads. Initial sample volume was 200 μl.
+cpm of [$^{125}$I]-goat anti-mouse IgG$_1$, IgG$_{2b}$, IgA and IgM × 10$^{-3}$ bound (1 × 10$^5$ cpm added) to HBsAg coated beads. Initial sample volume was 200 μl.
$^a$Double cloned hybridomas.
$^b$Single cloned hybridoma.
$^c$Complete media (see materials and methods) added for 24 hours to HBsAg coated beads followed by the second probes and incubated for an additional 24 hours.

We claim:

1. A process for preparing an antibody to a human viral hepatitis antigen which comprises intraperitoneally administering to an animal a first dosage of a hepatitis antigen in an amount of between approximately 1 and 50 μg/animal, intravenously administering a second dosage of the hepatitis antigen to said animal at least about 3 weeks after administering said first dosage, recovering lymphocyte cells producing antibody from said animal, forming cell hybrids by fusing said lymphocyte cells to a myeloma cell, culturing said hybrids and collecting said antibody as a product of said hybrids.

2. The process of claim 1 where the immunizing antigen is selected from the group consisting of Hepatitis B surface antigen (HBsAg), Hepatitis B core antigen (HBcAg), Hepatitis B e antigen (HBeAg), Hepatitis A virus (HAV), or viral antigens or non-A, non-B hepatitis virus(es).

3. The process of claim 1 wherein said hybrid is cultured in a histocompatable or immunocompromised animal and said antibody is recovered from the ascites fluid or serum of said animal.

4. The process of claim 1 wherein said hybrid is cloned and cultured in vitro.

5. The process of claim 3 wherein said hybrid is a clone.

6. The process of any one of claims 1, 2, 3, 4 or 5 wherein said lymphocyte cells are spleen cells.

7. The process of any one of claims 1, 2, 3, 4 or 5 wherein said lymphocyte cells are mouse spleen cells and said myeloma cells are mouse myeloma cells.

8. The process of any one of claims 1, 2, 3, 4 or 5 wherein said myeloma cells comprise mouse myeloma cells.

9. A compositon comprising a hybrid continuous cell line that produces antibody to a viral hepatitis antigen which comprises a cell hybrid of a BALB/c mouse spleen cell immunized with viral hepatitis antigen fused to a mouse myeloma and a culture medium for said hybrid.

10. The composition of claim 9 wherein said hybrid is located in a culture medium containing hypoxanthine-aminopterinthymidine.

11. The composition of any one of claims 9 or 10 wherein said antibody is an IgG fraction.

12. The composition of any one of claims 9 or 10 wherein said antibody is an IgM fraction.

13. The composition of any one of claims 9 or 10 wherein said antibody is an IgA fraction.

* * * * *